United States Patent
McClintock et al.

(10) Patent No.: US 9,545,270 B2
(45) Date of Patent: Jan. 17, 2017

(54) UNIVERSAL ROD HOLDER

(71) Applicant: K2M, Leesburg, VA (US)

(72) Inventors: Larry McClintock, Gore, VA (US); Kevin R. Strauss, Columbia, MD (US)

(73) Assignee: K2M, Inc., Leesbug, VA (US)

( * ) Notice: Subject to any disclaimer, the term of this patent is extended or adjusted under 35 U.S.C. 154(b) by 299 days.

(21) Appl. No.: 14/037,784

(22) Filed: Sep. 26, 2013

(65) Prior Publication Data
US 2014/0107706 A1    Apr. 17, 2014

Related U.S. Application Data

(60) Provisional application No. 61/706,230, filed on Oct. 15, 2012.

(51) Int. Cl.
*A61B 17/70* (2006.01)

(52) U.S. Cl.
CPC ....... *A61B 17/7083* (2013.01); *A61B 17/7002* (2013.01); *A61B 17/701* (2013.01)

(58) Field of Classification Search
CPC ............ A61B 17/7085; A61B 17/4086; A61B 17/7088; A61B 17/7083
See application file for complete search history.

(56) References Cited

U.S. PATENT DOCUMENTS

| | | | |
|---|---|---|---|
| 5,658,286 A | 8/1997 | Sava | |
| 5,910,141 A * | 6/1999 | Morrison | ........... A61B 17/7091 606/101 |
| 6,102,912 A | 8/2000 | Cazin et al. | |
| 6,319,257 B1 * | 11/2001 | Carignan | ............... A61F 2/4601 606/205 |
| 6,440,133 B1 | 8/2002 | Beale et al. | |
| 6,451,021 B1 | 9/2002 | Ralph et al. | |
| 6,582,434 B2 | 6/2003 | Kawakami et al. | |
| 6,644,087 B1 | 11/2003 | Ralph et al. | |
| 7,488,331 B2 | 2/2009 | Abdelgany | |
| 7,503,918 B2 | 3/2009 | Baccelli et al. | |
| 7,520,879 B2 | 4/2009 | Justis et al. | |
| 7,563,274 B2 | 7/2009 | Justis et al. | |
| 7,569,061 B2 | 8/2009 | Colleran | |
| 7,588,588 B2 | 9/2009 | Spitler et al. | |
| 7,604,653 B2 | 10/2009 | Kitchen | |
| 7,618,442 B2 | 11/2009 | Spitler et al. | |

(Continued)

*Primary Examiner* — Mary Hoffman
(74) *Attorney, Agent, or Firm* — Carter, DeLuca, Farrell & Schmidt, LLP

(57) ABSTRACT

A universal rod holder including a drive member and an elongated shaft member. The drive member has a proximal portion and a distal portion, and may include a handle disposed on the proximal portion, external threads disposed on the proximal portion of the drive member, and a tip disposed on a distal end of the distal portion of the drive member. The elongated shaft member includes a through hole, the through hole configured to receive the drive member, internal threads disposed on an inner surface of the through hole and configured to engage the external threads, and a hook member disposed on a distal end of the shaft member. The through hole extends into an opening of the hook member. The distal portion of the drive member is configured to slide through the through hole and into the opening of the hook member to secure a rod positioned therein.

14 Claims, 5 Drawing Sheets

(56) References Cited

U.S. PATENT DOCUMENTS

| | | | |
|---|---|---|---|
| 7,722,617 B2* | 5/2010 | Young | A61B 17/7086 606/86 A |
| 7,766,942 B2 | 8/2010 | Patterson et al. | |
| 7,931,676 B2 | 4/2011 | Veldman et al. | |
| 8,403,971 B2 | 3/2013 | Barrus et al. | |
| 2002/0161368 A1 | 10/2002 | Foley et al. | |
| 2003/0225408 A1 | 12/2003 | Nichols et al. | |
| 2006/0089651 A1* | 4/2006 | Trudeau | A61B 17/7086 606/86 R |
| 2007/0088362 A1* | 4/2007 | Bonutti | A61B 17/0218 606/99 |
| 2007/0093817 A1 | 4/2007 | Barrus et al. | |
| 2007/0191841 A1 | 8/2007 | Justis et al. | |
| 2007/0225712 A1 | 9/2007 | Altarac et al. | |
| 2008/0004629 A1* | 1/2008 | Nichols | A61B 17/7032 606/99 |
| 2008/0027432 A1 | 1/2008 | Strauss et al. | |
| 2008/0077136 A1* | 3/2008 | Triplett | A61B 17/7004 606/86 A |
| 2008/0086130 A1 | 4/2008 | Lake et al. | |
| 2008/0228233 A1* | 9/2008 | Hoffman | A61B 17/7088 606/86 A |
| 2009/0018593 A1 | 1/2009 | Barrus et al. | |
| 2009/0105716 A1 | 4/2009 | Barrus | |
| 2009/0105769 A1 | 4/2009 | Rock et al. | |
| 2009/0125032 A1* | 5/2009 | Gutierrez | A61B 17/7086 606/99 |
| 2009/0138044 A1 | 5/2009 | Bergeron et al. | |
| 2010/0114170 A1 | 5/2010 | Barrus et al. | |
| 2010/0121386 A1* | 5/2010 | Peultier | A61B 17/7086 606/86 A |
| 2010/0262196 A1 | 10/2010 | Barrus et al. | |
| 2012/0191144 A1* | 7/2012 | Peultier | A61B 17/7086 606/86 A |
| 2013/0144342 A1 | 6/2013 | Strauss et al. | |

* cited by examiner

UNIVERSAL ROD HOLDER

CROSS-REFERENCE TO RELATED APPLICATIONS

This application claims priority to, and the benefit of, U.S. Provisional Application Ser. No. 61/706,230 filed Sep. 27, 2012, the disclosure of which is hereby incorporated by reference in its entirety.

BACKGROUND

1. Technical Field

The present disclosure relates to a device for use in orthopedic surgeries and, more specifically, a universal rod holder for use during spinal surgery.

2. Discussion of Related Art

The spinal column is a complex system of bones and connective tissues that provide support for the human body and protection for the spinal cord and nerves. The adult spine includes twenty-four vertebral bodies, which are subdivided into three areas, including seven cervical vertebrae, twelve thoracic vertebrae and five lumbar vertebrae. Between adjacent vertebral bodies is an intervertebral disc that cushions and dampens the various translational and rotational forces exerted upon the spinal column.

There are various disorders, diseases and types of injury which the spinal column may experience in a lifetime. These problems may include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure to implant a rod or rods along the spine to support the vertebral bodies. Typically, the implanted rod is attached to the vertebral bodies using pedicle screws, hooks or anchors. Although instruments have been designed to assist in the insertion and/or manipulation of the rod into the implanted screws, hooks or anchors, there exists a need for a rod holder that can accommodate various rod diameters and shapes.

SUMMARY

In aspects of the present disclosure, a universal rod holder includes a drive member and an elongated shaft member. The drive member has a proximal portion and a distal portion, and may include a handle disposed on a proximal end of the drive member. The drive member may also have external threads disposed on the proximal portion of the drive member and a tip disposed on a distal end of the distal portion of the drive member. The elongated shaft member includes a through hole for receiving the drive member with internal threads disposed on an inner surface of the through hole which are configured to engage the external threads. A hook member is disposed on a distal end of the shaft member. The through hole extends through the shaft member and into an opening of the hook member. The distal portion of the drive member is configured to slide through the through hole and into the opening of the hook member.

In aspects of the present disclosure, the proximal portion of the drive member may have a first diameter that is larger than a diameter of the distal portion of the drive member. In aspects of the present disclosure, the universal rod holder may also be used with an anti-torque tool configured to releasably engage a neck portion of the shaft member. In aspects of the present disclosure, rotation of the drive member relative to the shaft member causes longitudinal movement of the distal portion of the drive member through the through hole.

In aspects of the present disclosure, the handle is a T-handle. In aspects of the present disclosure, the tip of the drive member includes a non-planar configuration. In aspects of the present disclosure, the universal rod holder, or any of the components thereof, is composed, entirely or partially, of a biocompatible material selected from a group consisting of: stainless steel, titanium, titanium alloys, polymers, and cobalt chrome.

In aspects of the present disclosure, a method for grasping a rod includes positioning a hook member of a shaft member around the rod, such that the rod is positioned within an opening of the hook member and against an internal wall of the hook member. The method also includes rotating a drive member to cause distal advancement of a tip of the drive member into the opening of the hook member and securing the rod between the internal wall of the hook member and the tip.

In aspects of the present disclosure, the method further includes coupling an anti-torque tool to the shaft member. In aspects of the present disclosure, the method further includes removing the drive member from the shaft member and inserting a second drive member into a through hole of the shaft member. The tip of the second drive member may be different from the tip of the first drive member.

In aspects of the present disclosure, a universal rod holder kit includes a shaft member having a through hole with internal threads disposed on an inner surface of the through hole and a hook member disposed on a distal end of the shaft member, and at least one drive member. The at least one drive member is configured to slide through the through hole and into an opening of the hook member to secure a rod positioned within the opening of the hook member. The at least one drive member includes external threads configured to threadingly engage the internal threads of the shaft member.

In aspects of the present disclosure, the kit includes a first drive member and a second drive member, where the respective tips of the first and second drive members have different shapes or sizes. In aspects of the present disclosure, a first tip of the first drive member includes a planar edge and the second tip of the second drive member includes a non-planar configuration. In aspects of the present disclosure, the kit further includes an anti-torque tool configured to engage the shaft member. In aspects of the present disclosure, the kit further includes a second shaft member having a second hook member.

BRIEF DESCRIPTION OF THE DRAWINGS

Various aspects of the present disclosure are described hereinbelow with reference to the drawings, wherein.

DETAILED DESCRIPTION

Figure 1:
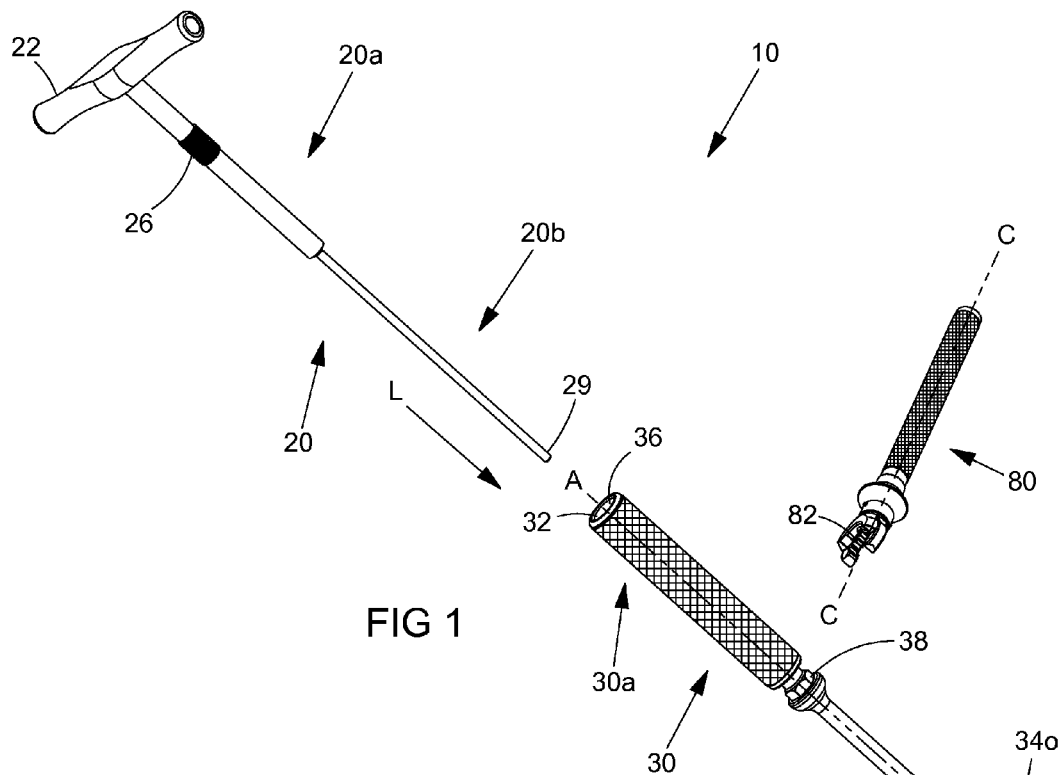
FIG. 1 is a perspective view of a universal rod holder, with parts separated, including a drive member and a shaft member, and an anti-torque tool, in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider or user and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure.

Figure 2:
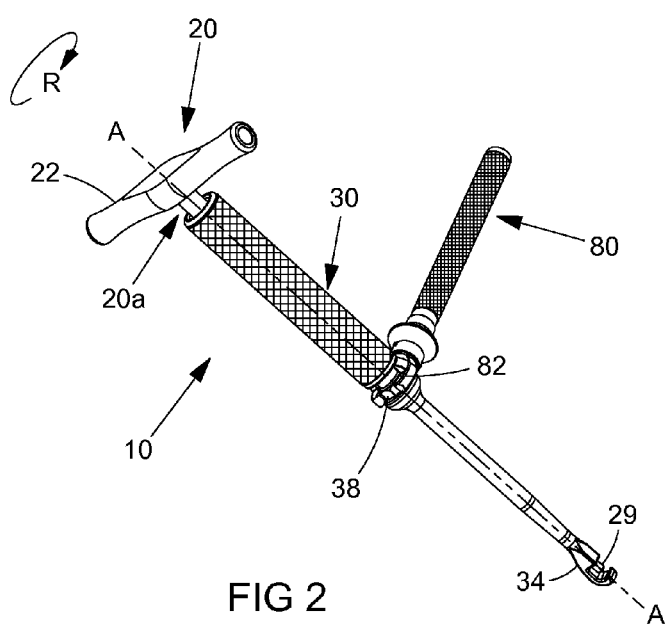
FIG. 2 is a perspective view of the universal rod holder and anti-torque tool of FIG. 1 coupled together.

With reference to FIGS. 1 and 2, a universal rod holder 10 is provided in accordance with the present disclosure including a drive member 20 and a shaft member 30. In embodiments, universal rod holder 10 may be used with an anti-torque tool 80. Shaft member 30 defines a longitudinal axis A-A and is configured to receive the drive member 20 therein. FIG. 1 illustrates the universal rod holder 10 with its components separated, and FIG. 2 illustrates universal rod holder 10 assembled, each of which will be described in detail below.

Figure 3A:
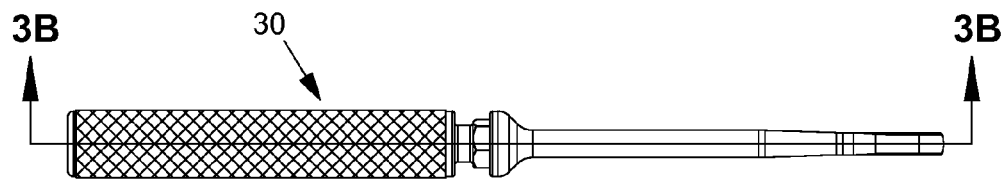
FIG. 3A is a top view of the shaft member of FIG. 1.
Figure 3B:
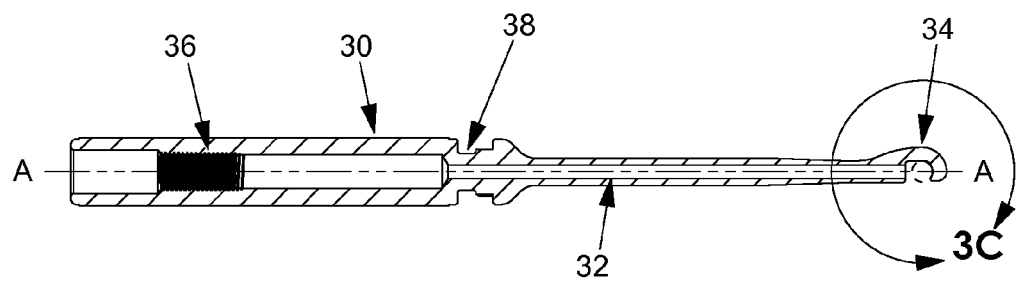
FIG. 3B is a side, cross-sectional, view of the shaft member taken along section line 3B-3B of FIG. 3A.
Figure 3C:
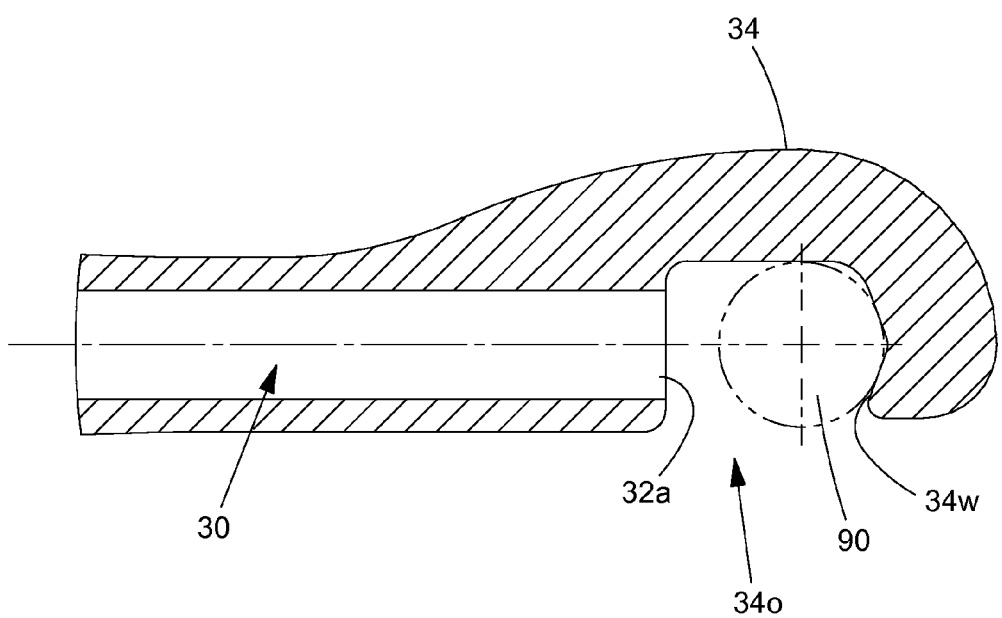
FIG. 3C is an enlarged view of the area of detail in FIG. 3B.

Continuing with reference to FIGS. 1 and 2, and additionally referring to FIGS. 3A-3C, shaft member 30 of universal rod holder 10 includes a proximal portion 30a and a distal portion 30b with a hook member 34 disposed on the distal portion 30b of the shaft member 30. Hook member 34 is configured to receive a rod 90 (FIG. 5A) therein, as will be described in further detail below. Shaft member 30 also includes a through hole 32 defining an internal passage extending along longitudinal axis A-A from the proximal portion 30a to the hook member 34. Through hole 32 includes internal threads 36 configured to threadingly engage the drive member 20, as will be discussed in further detail below.

Hook member 34 includes inner wall 34w defined on an inner surface thereof, and an opening 34o. Hook member 34 is configured to receive a rod 90 within opening 34o such that rod 90 may abut the inner wall 34w of hook member 34 when positioned therein. Through hole 32 extends through shaft portion 30, and in particular, from proximal portion 30a of shaft member 30 to an aperture 32a disposed on a distal portion 30b of the shaft member 30.

Internal threads 36 are formed on an internal surface of the through hole 32. In an aspect of the present disclosure, internal threads 36 are formed on an internal surface of through hole 32 within the proximal portion 30a of the shaft member 30. Although shown and described as being disposed in the proximal portion 30a, it is envisioned that internal threads 36 may be disposed on any portion of shaft member 30 within through hole 32, such as the distal portion 30b or any other portion of shaft member 30. Internal threads 36 are configured to threadingly engage external threads 26 of drive member 20 when drive member 20 is joined with shaft member 30 to secure drive member 20 to shaft member 30 and to axially advance drive member 20 along longitudinal axis A-A, as will be described in further detail below.

In aspects of the present disclosure, shaft member 30 further includes a neck portion 38 disposed between proximal portion 30a and distal portion 30b, for mating with an anti-torque tool 80, as will be described in further detail below.

Figure 4A:
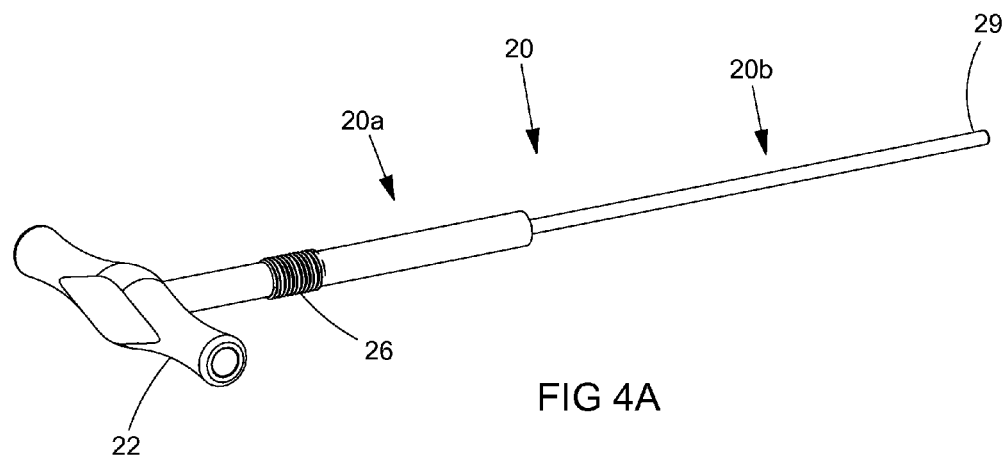
FIG. 4A is a perspective view of the drive member of FIG. 1.

With reference to FIGS. 1, 2, and 4A, drive member 20 of universal rod holder 10 includes a handle 22 disposed on the proximal end of a proximal portion 20a of the drive member 20 and tip 29 disposed on the distal end of a distal portion 20b of the drive member 20. Additionally, drive member 20 includes external threads 26 formed on an outer surface of the proximal portion 20a. Although illustrated and described as being formed on the proximal portion 20a of the drive member 20, it is envisioned that threads 26 may be formed on any portion of the drive member 20.

In aspects of the disclosure, handle 22 is a T-handle. However, it is envisioned that handle 22 may take any form of any type of gripping device suitable to perform the functions of a handle or provide leverage for rotating drive member 20 relative to the shaft member 30, i.e. about the longitudinal axis A-A of shaft member 30.

In aspects of the present disclosure, proximal portion 20a has a larger diameter than distal portion 20b. The external diameter of the proximal portion 20a of drive member 20 is substantially similar to the internal diameter of the proximal portion 30a of shaft member 30 (i.e., the diameter of a proximal portion of the through hole 32) and the outer diameter of distal portion 20b of drive member 20 is substantially similar to the inner diameter of aperture 32a.

External threads 26 of drive member 20 are configured to threadingly engage the internal threads 36 of shaft member 30.

Tip 29 of drive member 20 is configured to slide through the through hole 32 of shaft portion 30, and through the aperture 32a such that tip 29 is advanced into opening 34o of hook member 34 to engage a rod 90 (FIG. 5B) positioned therein, when the drive member 20 is advanced distally relative to the shaft member 30. In aspects of the disclosure, tip 29 of drive member 20 has a flat end or planar edge on its end.

Figure 4B:
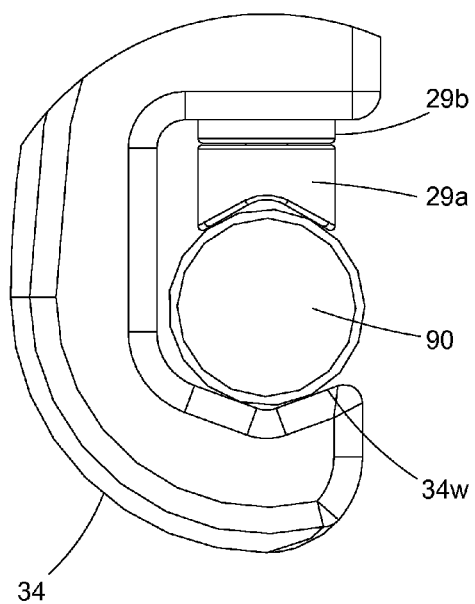
FIG. 4B is an end view of a rod secured to a hook member with a tip of a drive member having a non-planar configuration, in accordance with an embodiment of the present disclosure.
Figure 4C:
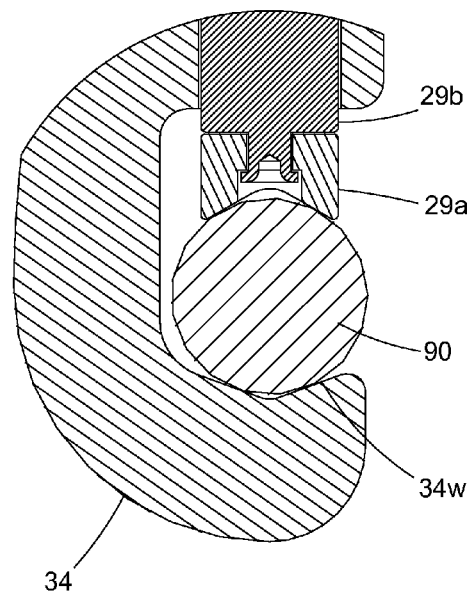
FIG. 4C is a cross-sectional view of FIG. 4B.

However, with particular reference to FIGS. 4B and 4C, in additional aspects of the present disclosure, a drive member 20 may have a tip 29a having a non-planar configuration to abut the outer surface of a rod 90 to be positioned within hook member 34. The non-planar configuration of the tip 29a may assist in providing more contact area between the tip 29a and the outer surface of the rod 90. Additionally, the non-planar configuration of the tip 29a may reduce any potential for inducing stress on the rod 90 and/or the drive member 20. Tip 29a is operably coupled to a coupling portion 29b disposed on the distal portion 20b of the drive member 20, such that the drive member 20 may be axially rotated relative to the tip 29a when the tip 29a abuts the outer surface of rod 90 and the outer surface of rod 90 is fully seated within the tip 29a as shown in FIGS. 4B and 4C.

The non-planar configuration of tip 29a may be V-shaped or may have an arcuate configuration. Alternatively, the non-planar configuration of tip 29a may be a compound curve defined by separate sections, each section having a different radius curvature. In this respect, the plurality of radii of curvature defines a compound curve that provides two or more lines of contact on a plurality of different diameter rods 90. In one instance, the tip 29a has three adjacent sections and each section has a radius of curvature that is different from the other two sections. It is contemplated that the compound curvature is symmetrical about a central longitudinal axis that extends through the tip 29a and the drive member 20.

With reference to FIGS. 1-4A, it is envisioned that in some aspects of the present disclosure, the universal rod holder 10 is pre-assembled with the drive member 20 already coupled to the shaft member 30. However, in other aspects of the present disclosure, a kit may be provided including multiple drive members and/or multiple shaft members, each having different shapes and/or sizes. For example, in one aspect, the kit may include one shaft member 30 with two drive members, where one drive member has a tip 29 with a planar edge (FIG. 4A) and the other drive member has a tip 29a with a non-planar configuration (FIGS. 4B and 4C). In another aspect of the present disclosure, the kit may include additional drive members and/or shaft members. The additional shaft member may have respective hook member of different shapes and/or sizes. Additionally, a kit may include multiple assembled universal rod holders, for example one assembled universal rod holder with a drive member 20 having a tip 29 (FIG. 4A) and a second assembled universal rod holder with a drive member 20 having a tip 29a (FIG. 4B).

With reference back to FIG. 1, the kit may require assembly of the universal rod holder. Assembly includes inserting one of the drive members 20 into one of the shaft members 30, provided in the kit, through the through hole 32 in the direction of arrow "L" and distally advancing the drive member 20 through shaft member 30 until external threads 26 of drive member 20 contact internal threads 36 of shaft member 30. Once external threads 26 are positioned proximate the internal threads 36, drive member 20 is rotated about the longitudinal axis A-A in the direction of arrow "R" to threadingly engage the external threads 26 with the internal threads 36 and to cause further distal advancement of the drive member 20 through the through hole 32 along the longitudinal axis A-A. Although shown and described as being rotated in the direction of arrow "R," it is envisioned that the external threads 26 and the internal threads 36 may be arranged such that rotation of the drive member 20 in the direction opposite of arrow "R" causes threaded engagement and causes distal advancement of the drive member 20 through the through hole 32. Distal advancement of the drive member 20 through the through hole 32 causes corresponding distal advancement of the tip 29 through the through hole 32, and eventually causes the tip 29 to extend beyond, or otherwise protrude from, the aperture 32a to enter the opening 34o of the hook member 34. When a rod 90 is positioned within the opening 34o of the hook member 34, the tip 29 is advanced distally until the rod 90 abuts the inner wall 34w and is secured against the inner wall 34w.

In aspects of the present disclosure, universal rod holder 10 is usable with an anti-torque tool 80 (FIGS. 1 and 2) and shaft member 30 includes a neck portion 38 disposed between the proximal portion 30a and the distal portion 30b. Neck portion 38 is configured to mate with receiving member 82 of anti-torque tool 80 to couple anti-torque tool 80 to shaft member 30. Neck portion 38 of shaft member 30 and receiving member 82 of anti-torque tool 80 include corresponding structure configured to releasably couple the anti-torque tool 80 to the shaft member 30. Receiving member 82 includes an open end such that neck portion 38 may be received within the open end of receiving member 82. In embodiments, anti-torque tool 80 defines longitudinal axis C-C, which is perpendicular to longitudinal axis A-A defined by shaft member 30. To this end, when anti-torque tool 80 is coupled to shaft member 30, anti-torque tool 80 may be used as a leverage device to prevent rotation of the shaft member 20 in a direction orthogonal to longitudinal axis A-A when the drive member 20 is rotated in the direction of arrow "R."

Figures 5A, 5B:
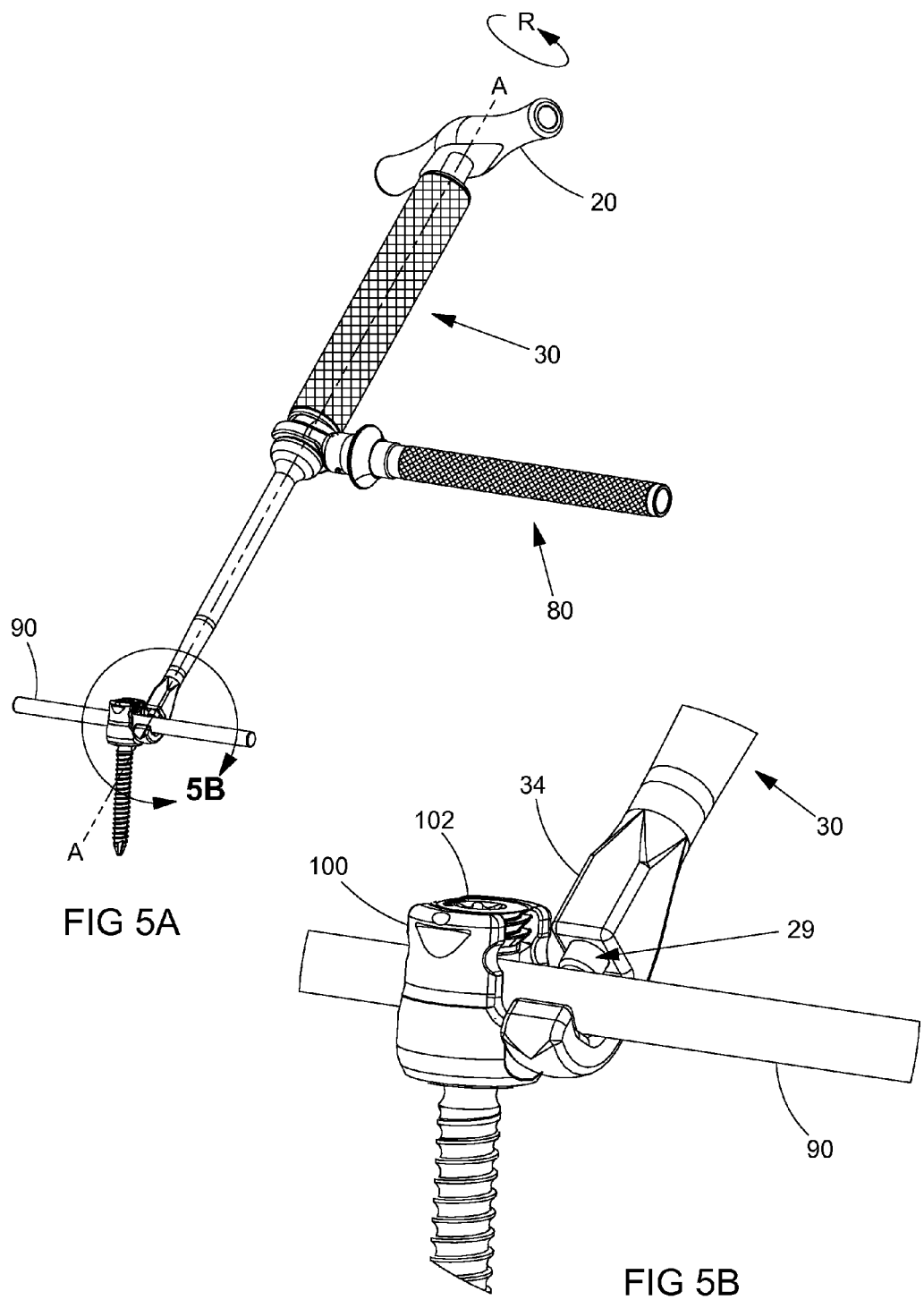
FIG. 5A is a perspective view of the universal rod holder of FIG. 1 grasping a rod.
FIG. 5B is an enlarged view of the area of detail in FIG. 5A.
Figure 6A:
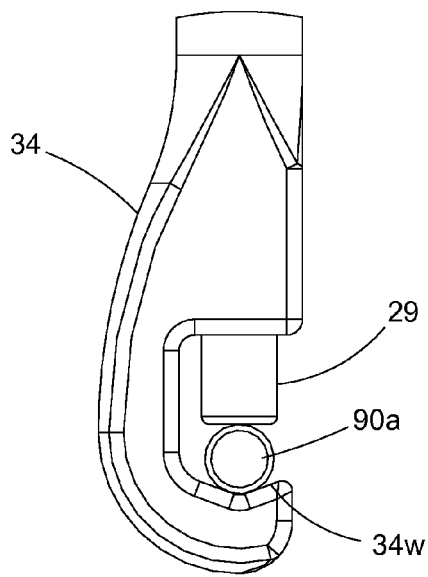
FIG. 6A is an end view of the hook member of the universal rod holder of FIG. 1 with a rod positioned therein.
Figure 6B:
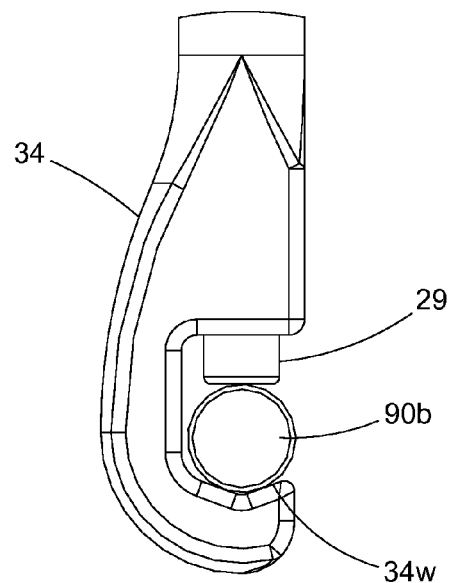
FIG. 6B is an end view of the hook member of FIG. 6A securing a rod having another size.
Figure 6C:
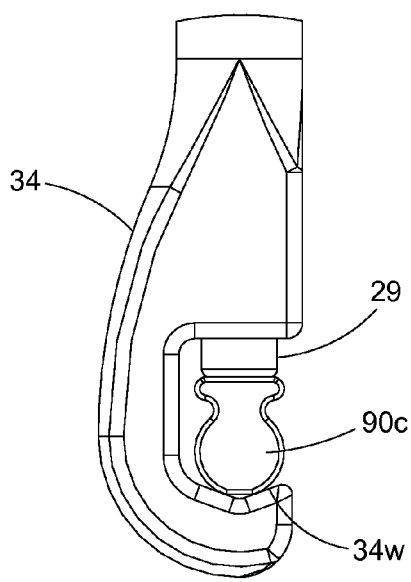
FIG. 6C is an end view of the hook member of FIG. 6A securing a rod having another shape and size.
Figure 6D:
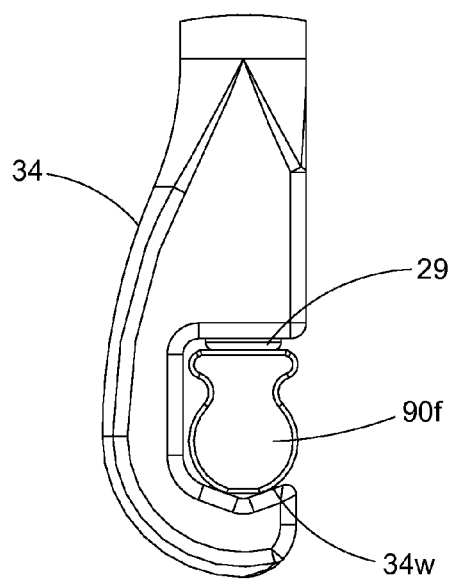
FIG. 6D is an end view of the hook member of FIG. 6C securing a rod having another size.

Turning now to FIGS. 5A and 5B, use of the universal rod holder 10 will now be described. As described above, during assembly, a user inserts the distal portion 20b, i.e. the tip 29, of drive member 20 distally into the through hole 32 of the shaft member 30. As described above, once the external threads 26 of drive member 20 are positioned proximate the internal threads 36 of the shaft member 30, a user rotates the drive member 20 in the direction of arrow "R" to cause the external threads 26 to threadingly engage the internal threads 36 and to further distally advance the drive member 20 relative to the shaft member 30.

Once assembled, i.e. once the drive member 20 is threadingly engaged to the shaft member 30, the hook member 34 is then coupled to, or positioned about, the rod 90. In particular, the rod 90 is positioned within the opening 34o of the hook member 34 and the outer surface of the rod 90 is positioned against the inner wall 34w of hook member 34. Although described in this order, it is envisioned, that the hook member 34 may be positioned about the rod 90 prior to insertion of the drive member 20 within the shaft member 30. To this end, a user may desire to place the hook member 34 about the rod 90 and then subsequently couple the drive member 20 to the shaft member 30.

Subsequent to placement of the rod 90 within the hook member 34, i.e., against the inner wall 34w, the drive member 20 is further distally advanced along the longitudinal axis A-A relative to the shaft member 30 to secure the rod 90 within the hook member 34. In particular, a user restricts the rotational movement of the shaft member 30 such that when the drive member 20 is rotated in the direction of arrow "R," the drive member 20 advances distally relative to the shaft member 30. The drive member 20 is continuously rotated in this manner until the tip 29 extends through the aperture 32a and into the opening 34o of the hook member 34. Once the tip 29 extends through the aperture 32a, the user continues to rotate the drive member 20 relative to the shaft member 30 until the tip 29 comes into contact with the rod 90 that is positioned against the inner wall 34w of the hook member 34.

Once the rod 90 is secured to the universal rod holder 10, i.e., the rod 90 is secured to the hook member 34 between the inner wall 34w of the hook member 34 and the tip 29 of the drive member 20, the universal rod holder 10 may be manipulated to control movement of the rod 90 attached thereto. In aspects of the present disclosure, the universal rod holder 10 is manipulated to insert the rod 90 into a screw housing 100 (FIG. 5B) of a pedicle screw. Once inserted into the screw housing 100, the rod 90 is held in place until the rod 90 is locked in place with a set screw 102 of the screw housing 100. The pedicle screw may be a set screw style pedicle screw as shown or may also be a taper lock type pedicle screw as disclosed in commonly owned U.S. application Ser. No. 12/739,461, published as U.S. Patent Application Publication No. 2010/0262196, the entire contents of which is incorporated by reference herein. Another example of a suitable pedicle screw is shown and disclosed in commonly owned U.S. Pat. No. 8,403,971.

If desired, a user may also attach anti-torque tool 80 to the shaft member 30 to assist the user in restricting the rotational movement of the shaft member 30 when the drive member 20 is rotated relative to the shaft member 30. Additionally, the anti-torque tool 80 may assist a user in movement of the rod 90, after the rod 90 is secured to the universal rod holder 10, relative to a screw or hook inserted in a vertebra.

In aspects of the present disclosure, the universal rod holders described above, and any of the components thereof, may be constructed of a variety of biocompatible materials, e.g., stainless steel, cobalt chrome, PEEK, titanium, titanium alloys, etc.

Referring now to FIGS. 6A-6D, various rods 90a-90d, referred to collectively as rods 90, are illustrated being secured to hook member 34. The diameters and shapes of the rods 90 that may be secured to universal rod holder 10 (FIG. 1) may vary. In one aspect of the present disclosure, rods 90 have diameters that range from 3.0 mm to 8.0 mm.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, any components of each of the embodiments described may be used with any of the other embodiments described.

What is claimed:

1. A universal rod holder comprising:
   a drive member having a proximal portion and a distal portion, the drive member including:
      a handle disposed on the drive member;
      external threads disposed on the proximal portion of the drive member; and
      a tip disposed on a distal end of the distal portion of the drive member;
   a shaft member including a through hole having an aperture at a distal end of the shaft, the through hole configured to receive the drive member in a coaxial arrangement;
   internal threads disposed on an inner surface of the through hole, the internal threads configured to engage the external threads; and
   a hook member disposed on a distal end of the shaft member, the hook member having an opening transverse to the aperture, wherein the distal portion of the drive member is configured to slide through the through hole such that the tip of the drive member is proximate an inner wall of the hook member.

2. The universal rod holder according to claim 1, wherein the proximal portion of the drive member has a first diameter and the distal portion of the drive member has a second diameter, wherein the first diameter is larger than the second diameter.

3. The universal rod holder according to claim 1, further including an anti-torque tool, wherein the shaft member includes a neck portion configured to releasably engage the anti-torque tool.

4. The universal rod holder according to claim 1, wherein rotation of the drive member relative to the shaft member causes longitudinal movement of the distal portion of the drive member through the through hole.

5. The universal rod holder according to claim 1, wherein the tip of the drive member has a non-planar configuration.

6. The universal rod holder according to claim 1, wherein the tip of the drive member has a planar configuration.

7. The universal rod holder according to claim 3, wherein engagement of the shaft member with the anti-torque tool inhibits rotation of the shaft member in a direction orthogonal to a longitudinal axis of the drive member.

8. The universal rod holder according to claim 1, wherein the opening of the hook member is configured to receive a spinal rod therethrough and the inner wall is configured to receive the spinal rod thereon.

9. The universal rod holder according to claim 3, wherein the anti-torque tool defines a receiving member, and the neck portion of the shaft member is disposed between a proximal portion and a distal portion thereof, the receiving member of the anti-torque tool includes an open end to selectively receive the neck portion therein.

10. The universal rod holder according to claim 1, wherein the hook member defines a generally "C" shape.

11. The universal rod holder according to claim 1, wherein a longitudinal axis of the shaft member is transverse to the opening of the hook member.

12. The universal rod holder according to claim 1, wherein the shaft member includes a proximal portion, a distal portion, and the through hole extends therebetween.

13. The universal rod holder according to claim 1, wherein the shaft member, the through hole, the aperture, and the drive member are configured to define a coaxial arrangement.

14. The universal rod holder according to claim 1, wherein the aperture and the through hole of the shaft member are in communication with the opening of the hook member.

* * * * *